(12) United States Patent
Pourreau et al.

(10) Patent No.: US 6,780,951 B2
(45) Date of Patent: Aug. 24, 2004

(54) MULTIFUNCTIONAL ALLYL CARBAMATES AND COATINGS THEREFROM

(75) Inventors: Daniel B. Pourreau, Exton, PA (US); Peter J. Whitman, Glen Mills, PA (US); Stephen L. Goldstein, Glen Mills, PA (US); Stephen H. Harris, Kennett Square, PA (US)

(73) Assignee: Arco Chemical Technology, L.P., Greenville, DE (US)

( * ) Notice: Subject to any disclaimer, the term of this patent is extended or adjusted under 35 U.S.C. 154(b) by 0 days.

(21) Appl. No.: 10/314,608

(22) Filed: Dec. 9, 2002

(65) Prior Publication Data

US 2003/0130469 A1 Jul. 10, 2003

Related U.S. Application Data

(62) Division of application No. 09/706,629, filed on Nov. 6, 2000, now Pat. No. 6,555,596.

(51) Int. Cl.[7] .................. C08L 75/16; C08L 75/14; C08G 18/67; C08J 3/28
(52) U.S. Cl. .................. 526/301; 526/302; 526/310; 525/123; 525/127; 525/330.5; 525/452; 528/49; 528/75; 260/25; 260/26; 260/115; 260/158
(58) Field of Search .................. 522/90, 96, 95, 522/174, 173, 150, 152; 526/301, 302, 310; 525/123, 127, 330.5, 452; 528/49, 75; 560/25, 26, 115, 158

(56) References Cited

U.S. PATENT DOCUMENTS

| | | | |
|---|---|---|---|
| 29,772 A | * 8/1860 | Niederhauser et al. .......... 76/62 |
| 2,483,194 A | * 9/1949 | Gleim .......... 826/232 |
| 2,926,148 A | * 2/1960 | Rene et al. .......... 528/74.5 |
| 3,268,561 A | 8/1966 | Peppel et al. .......... 260/348 |
| 3,666,133 A | * 5/1972 | Benning .......... 220/560.02 |
| 3,876,729 A | * 4/1975 | Mueller .......... 525/276 |
| 4,005,041 A | * 1/1977 | Piggott .......... 528/73 |
| 4,031,271 A | * 6/1977 | Bush .......... 427/273 |
| 4,100,143 A | * 7/1978 | Wolf et al. .......... 524/235 |
| 4,119,510 A | * 10/1978 | Williams .......... 522/174 |
| 4,126,747 A | 11/1978 | Cowherd, III et al. .......... 520/166 |
| 4,160,080 A | * 7/1979 | Koenig et al. .......... 528/59 |
| 4,279,833 A | * 7/1981 | Culbertson et al. .......... 558/393 |
| 4,433,179 A | * 2/1984 | Lohse et al. .......... 548/302.7 |
| 4,614,761 A | * 9/1986 | Takiyama et al. .......... 525/293 |
| 4,618,703 A | 10/1986 | Thanawalla et al. .......... 560/209 |
| 4,829,123 A | * 5/1989 | Shigematsu et al. .......... 525/28 |
| 4,929,403 A | * 5/1990 | Audsley .......... 264/129 |
| 5,030,696 A | * 7/1991 | DuPont et al. .......... 525/278 |
| 5,049,623 A | * 9/1991 | Dupont .......... 428/424.2 |
| 5,075,384 A | * 12/1991 | DuPont et al. .......... 525/278 |
| 5,089,586 A | * 2/1992 | Piepho et al. .......... 528/75 |
| 5,198,528 A | * 3/1993 | Smith et al. .......... 106/252 |
| 5,236,978 A | * 8/1993 | Selvig et al. .......... 524/81 |
| 5,274,067 A | * 12/1993 | Kressdorf et al. .......... 528/75 |
| 5,356,669 A | 10/1994 | Rehfuss et al. .......... 427/407 |
| 5,451,631 A | 9/1995 | Guo et al. .......... 524/529 |
| 5,461,135 A | 10/1995 | Malofsky et al. .......... 528/60 |
| 5,525,693 A | 6/1996 | Guo .......... 526/329.2 |
| 5,552,486 A | * 9/1996 | Guo et al. .......... 525/118 |
| 5,610,252 A | * 3/1997 | Bambury et al. .......... 526/245 |
| 5,709,950 A | 1/1998 | Burgman et al. .......... 428/423.1 |
| 5,739,251 A | * 4/1998 | Venham et al. .......... 252/182.18 |
| 5,763,099 A | * 6/1998 | Misev et al. .......... 428/482 |
| 6,011,080 A | 1/2000 | Daly et al. .......... 522/107 |
| 6,075,108 A | 6/2000 | Guo .......... 526/312 |
| 6,114,402 A | * 9/2000 | Smith .......... 252/182.2 |
| 6,156,861 A | * 12/2000 | Guo .......... 526/312 |
| 6,355,838 B1 | * 3/2002 | Huffman et al. .......... 560/156 |
| 6,559,260 B1 | * 5/2003 | Fan et al. .......... 526/301 |

FOREIGN PATENT DOCUMENTS

| | | | |
|---|---|---|---|
| EP | 0059561 | * 8/1982 | |
| EP | 356847 A2 | * 3/1990 | .......... C08F/299/06 |
| EP | 356848 A2 | * 3/1990 | .......... C08R/299/06 |
| WO | WO0172862 | * 10/2001 | |

OTHER PUBLICATIONS

*Bulk Free Radical Copolymerization of Allylic Alcohol with Acrylate and Styrene Comonomers*, Shao–Hau Guo, 1998 American Chemical Society (113–126).

* cited by examiner

Primary Examiner—James J. Seidleck
Assistant Examiner—Sanza L. McClendon
(74) Attorney, Agent, or Firm—Shao-Hua Guo

(57) ABSTRACT

Allyl carbamates are disclosed. The allyl carbamates are prepared by reacting an isocyanate with an allylic alcohol or alkoxylated allylic alcohol. Suitable isocyanates are selected from hexamethylene diisocyanate (HDI), HDI biuret, dimer, HDI trimer, HDI allophanate, isophorone diisocyanate (IPDI), IPDI trimer, IPDI allophanate, bis(isocyanatocyclohexyl)methane, and mixtures thereof. The allyl carbamates have at least two allyl functional groups per molecule. UV-curable and air-drying coatings formulated from the allyl carbamates show excellent chemical resistance and physical properties.

3 Claims, No Drawings

MULTIFUNCTIONAL ALLYL CARBAMATES AND COATINGS THEREFROM

This application is a division of application Ser. No. 09/706,629, filed on Nov. 6, 2000 now U.S. Pat. No. 6,555,596.

FIELD OF THE INVENTION

The invention relates to multifunctional allyl carbamates. More particularly, the invention relates to multifunctional allyl carbamates that are useful for air-drying and UV-curable coatings.

BACKGROUND OF THE INVENTION

Allyl monomers hardly homopolymerize but readily copolymerize with vinyl and acrylate monomers. They are strong chain transfer agents and give the copolymers low molecular weights. This unique characteristic has led to the development of a variety of copolymers of allyl alcohol or alkoxylated allyl alcohols with vinyl aromatics (see, e.g., U.S. Pat. No. 5,451,631) and acrylates (see, e.g., U.S. Pat. No. 5,525,693). These copolymers are characterized by an even distribution of hydroxyl groups. See S. Guo, *Solvent Free Polymerization and Process*, ACS series book, 713, Chapter 7, pp.113–126(1998).

More recently, copolymers of allyl carbamates with vinyl aromatics and acrylates have been disclosed. See U.S. Pat. No. 6,075,108. The '108 patent teaches monofunctional allyl carbamates, i.e., the monomers have only one allyl functional group per molecule. The copolymers are thermoplastic resins with pendant carbamate functional groups. The carbamate groups can then react with crosslinking agents such as melamine resins to form thermoset coatings.

Multifunctional acrylate carbamates are also known. (See, e.g., U.S. Pat. No. 4,126,747.) These multifunctional monomers are crosslinked through the acrylate groups by photo-oxidation or a free-radical reaction. Introducing carbamate groups into coatings can potentially enhance acid etch resistance, adhesion, durability, and other performance features. (See, e.g., U.S. Pat. Nos. 5,356,669 and 5,709,950).

Multifunctional allyl carbamates are of interest because they improve crosslink density and coating performance. Importantly, these monomers should give derivative coatings uniform network structures.

SUMMARY OF THE INVENTION

The invention relates to allyl carbamates. The allyl carbamates are reaction products of an isocyanate and an allylic alcohol or alkoxylated allylic alcohol. The isocyanates are selected from hexamethylene diisocyanate (HDI), HDI biuret, HDI dimer, HDI trimer, HDI allophanate, isophorone diisocyanate (IPDI), IPDI trimer, IPDI allophanate, bis(isocyanatocyclohexyl)methane, and the like, and mixtures thereof.

The invention includes air-drying and UV (ultraviolet light)-curable coatings that comprise the allyl carbamates. The invention further includes UV-curable powder coatings that comprise solid allyl carbamates and solvent-free air-drying and UV-curable coatings that comprise liquid allyl carbamates. The coatings have excellent chemical resistance and weathering stability.

DETAILED DESCRIPTION OF THE INVENTION

The allyl carbamates of the invention are prepared by reacting an isocyanate with an allylic alcohol or alkoxylated allylic alcohol. The isocyanates are selected from hexamethylene diisocyanate (HDI), HDI biuret, HDI dimer, HDI trimer, HDI allophanate, isophorone diisocyanate (IPDI), IPDI trimer, IPDI allophanate, bis(isocyanatocyclohexyl) methane, and the like, and mixtures thereof. These isocyanates are commercially available, for example, from Lyondell Chemical Company.

Methods for preparing HOI and IPDI allophanates are known. For example, U.S. Pat. No. 5,461,135, the teachings of which are incorporated herein by reference, teaches the preparation of allophanates. In one method, HDI allophanate is prepared by: (1) dimerizing HDI in the presence of tributyl phosphine to convert about 10% of the HDI to uretidione oligomers, (2) adding a suitable amount of diethylene glycol to the mixture to reach about 20 wt % of uretidione content, and then (3) adding an equivalent amount of methyl tosylate to terminate the reaction. Suitable HDI and IPDI allophanates preferably have an NCO functionality from 2.8 to 6.5, an NCO content from 10 to 47 wt %, a viscosity less than 1000 cps at 25° C., and a molar ratio of uretidione to allophanate from about 20:1 to about 1:5.

Allylic alcohols for use in the invention have the general structure:

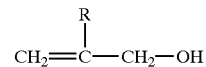

in which R is hydrogen, $C_1$ to $C_{10}$ alkyl, or $C_6$ to $C_{10}$ aryl or alkylaryl. Suitable allylic alcohols include, for example, allyl alcohol, methallyl alcohol, 2-ethyl-2-propen-1-ol, 2-pentyl-2-propen-1-ol, and the like, and mixtures thereof.

Suitable alkoxylated allylic alcohols have the structure:

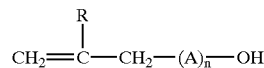

in which A is a $C_2$–$C_4$ oxyalkylene group, and n, which is the average number of oxyalkylene units in the alkoxylated allylic alcohol, has a value within the range of 1 to about 5; preferably n is 1 to about 2. Suitable alkoxylated allylic alcohols include propoxylated allylic alcohols, ethoxylated allylic alcohols, butoxylated allylic alcohols, and the like, and mixtures thereof. Suitable alkoxylated allylic alcohols also include those having a mixture of oxyalkylene units such as oxypropylene, oxyethylene and oxybutylene. Suitable alkoxylated allylic alcohols can be made, for example, by reacting an allylic alcohol with an alkylene oxide. For example, U.S. Pat. Nos. 3,268,561 and 4,618,703, the teachings of which are incorporated herein by reference, teach how to make propoxylated allylic alcohol.

The reaction of the isocyanate with the allylic alcohol or alkoxylated allylic alcohol is preferably performed at an elevated temperature. The reaction temperature is preferably within the range of 60° C. to 160° C. A catalyst can be used to shorten reaction time, to lower the reaction temperature, or both. Suitable catalysts include tertiary amine and organotin compounds. Examples of organotin catalysts are stannous octoate and dibutyltin dilaurate. The catalyst is used in an amount less than 1 wt % of the total product. A solvent can also be used to control the reaction or lower the viscosity of the reaction mixture. Suitable solvents include ethers, esters, ketones, aromatic and aliphatic hydrocarbons, glycol ether esters, and the like, and mixtures thereof. Excess allylic alcohol or alkoxylated allylic alcohol is used to convert essentially all of the isocyanate (NCO) groups to carbamates. The small excess of allylic compounds can be removed after the reaction although they typically do not interfere with coating properties. Conversion of the NCO group to a carbamate group can be monitored by infrared spectroscopy (IR). The allyl carbamate products have an average allyl functionality of at least 2.

The invention includes UV-curable coatings that comprise the allyl carbamates. The allyl carbamates can be used as crosslinking agents in amounts preferably less than about 10 wt % of the total coating composition or as primary components in amounts preferably greater than about 10 wt % of the total coating composition.

The UV-curable coating preferably comprises a UV-curable monomer or oligomer that is capable of copolymerizing with the allyl carbamate. Examples of suitable monomers are decyl acrylate, ethoxyethyl acrylate, 2-ethylhexyl acrylate, 2-ethylhexylvinyl ether, hexyl acrylate, isodecyl acrylate, isooctyl acrylate, isobornyl acrylate, lauryl acrylate, lauryl vinyl ether, N-vinylformamide, N-vinylpyrrolidone, stearylacrylate, N-vinylcaprolactam, and the like, and mixtures thereof.

Examples of suitable oligomers are polyethylene glycol acrylate or methacrylate, polypropylene glycol acrylate or methacrylate, polyester acrylates or methacrylates, urethane acrylates or methacrylates, epoxy acrylates or methacrylates, and the like, and mixtures thereof.

Suitable UV-curable monomers or oligomers also include those having two or more UV-curable functional groups capable of copolymerizing with the allyl carbamates. Examples are polyethylene glycol diacrylate or dimethacrylate, 1,6-hexanediol divinylether, pentaerythritol triacrylate, ethoxylated bisphenol-A diacrylate, tripropyleneglycol diacrylate, unsaturated polyesters such as those prepared from maleic anhydride, fumaric acid, or itaconic acid or anhydride, and the like, and mixture thereof. The UV-curable monomers or oligomers are used in amounts preferably from about 50 wt % to about 95 wt % of the total coating formulation.

The UV-curable coatings, comprise a photoinitiator. Examples of suitable photoinitiators are hydroxycyclohexylphenyl ketone, hydroxymethylphenylpropanone, dimethoxyphenylacetophenone, 2-methyl-1-[(4-methylthio)-phenyl]-2-morphol inopropan-1-one, 1-(4-isopropylphenyl)-2-hydroxy-2-methylpropan-1-one, 1-(4-dodecyl-phenyl)-2-hydroxy-2-methylpropan-1-one, 4-(2-hydroxyethoxy)phenyl-2(2-hydroxy-2-propyl)ketone, diethoxyphenyl acetophenone, 2,4,6-trimethylbenzoyl diphenylphosphine oxide, a mixture of (2,6-dimethoxy berizoyl)-2,4,4-trimethylpentylphosphine oxide and 2-hydroxy-2-methyl-1-phenyl-propan-1-one, benzophenone, and the like, and mixtures thereof. The amount of photoinitiator is typically less than about 10 wt % of the coating formulation, and preferably within the range of about 1 wt % to about 5 wt %.

Optionally, free radical initiators, such as organic peroxides and azo compounds, can also be employed in addition to photoinitiators. Using free radical initiators can enhance curing down near the substrate, particularly when pigmented, opaque, or thicker film coatings are desired. Examples of suitable free radical initiators are benzoyl peroxide, t-butyl perbenzoate, 2,2'-azobis[isobutyronitrile], t-butylhydroperoxide, and di-t-butyl peroxide. The amount of free radical initiator is preferably less than about 5 wt % of the coating formulation. Optionally, pigments, fillers, flow control agents, light stabilizers and many other commonly used coating additives are also used.

Preferably, the UV-curable coating composition also contains a metal dryer capable of accelerating oxidative curing of the allyl carbamates and enhancing the rate of UV-curing. This provides a "dual-cure" mechanism for the coating that both reduces the amount of UV-radiation required to fully cure the system and cure parts of the coating that receive either no UV-light or insufficient light. This is particularly useful when curing UV-coatings applied to three-dimensional parts such as wood, plastic, or metal parts, especially automotive parts and bodies.

The invention includes liquid UV-curable coatings. Preferably, the liquid coatings contain no solvent. Preferred allyl carbamates for solvent-free UV-curable coatings are those which are liquids at 25° C., especially those having low viscosity. If desirable, however, an organic solvent can be added into the formulation to adjust the viscosity. Suitable solvents include alcohols, ethers, esters, glycol ethers, glycol ether esters, aliphatic and aromatic hydrocarbons. Particularly useful solvents are those which are negligibly reactive with hydroxyl radical and do not contribute appreciably to the formation of ground-based ozone. Some of these solvents have been exempted from the list of the Volatile Organic Compound (VOC) by the U.S. Environmental Protection Agency (EPA) or have been proposed for exemption. Examples of solvents that are VOC-exempt or proposed for exemption include p-chlorobenzotrifluoride, acetone, methyl acetate and tertiary-butyl acetate.

The UV-curable coatings can be applied by any known techniques, e.g., spray and roll coat. They are exposed to UV light and then cured. Suitable UV sources include standard medium pressure mercury-, iron doped mercury-, and/or gallium doped mercury-vapor lamps. Electron beam radiation may be used instead of UV radiation, if desired. The curing takes from about 0.001 to about 10 seconds, and typically less than about 3 seconds.

The invention also includes UV-curable powder coatings. The UV-curable powder coatings comprise a solid allyl carbamate. Preferably, the allyl carbamate has a glass transition temperature ($T_g$) of at least 40° C. UV-curable powder coatings are relatively new but known in the art. For example, U.S. Pat. No. 6,011,080, the teachings of which are incorporated herein by reference, teaches how to prepare an unsaturated polyester-based powder coating.

The invention includes an air-drying coating that comprises the allyl carbamate. The coating optionally includes an air-drying alkyd resin and an air-drying catalyst. Any known air-drying alkyd resin can be used. Air-drying alkyd resins can be produced by reacting a polyfunctional alcohol, a polyfunctional acid (or acid anhydride) and an oxidizing oil or fatty acid. Polyfunctional alcohols that can be used in preparing the alkyd resins include glycerine, trimethylolethane, trimethylolpropane, pentaerythritol, sorbitol, mannitol, ethylene glycol, diethylene glycol, and similar polyols. Pentaerythritol and glycerine are preferred polyfunctional alcohols. Polyfunctional acids which can be used in preparing the alkyds include phthalic, maleic, fumaric, isophthalic, succinic, trimellitic, adipic, azelaic, and sebacic acids, as well as the anhydrides of such acids, and the like, and mixtures thereof.

Suitable oils for preparing the alkyd are drying or semi-drying oils. Examples are linseed, soya, safflower, perilla, tung, oiticica, and poppyseed oils and the like, and mixtures thereof. The above oils can also be used in the form of fatty acids.

Suitable alkyd resins also include fatty esters of styrene-allyl alcohol or styrene-allyl propoxylate copolymers. For example, U.S. Pat. No. 5,451,631, the teachings of which are incorporated herein by reference, teaches how to prepare an alkyd by condensation of a vinyl aromatic/propoxylated allyl alcohol copolymer with an unsaturated fatty acid.

The air-drying coating comprises a drying catalyst such as cobalt octoate. Optionally, free radical initiators, such as organic peroxides and azo compounds, can also be employed in addition to the drying catalyst. Examples of suitable free radical initiators are discussed above.

Optionally, the air-drying coating also comprises a solvent. Suitable solvents are discussed above. The coating solution is spread or drawn down onto a surface, the solvent evaporates, and the resin cures.

The following examples merely illustrate the invention. Those skilled in the art will recognize many variations that are within the spirit of the invention and scope of the claims.

EXAMPLE 1

Preparation of Allyl Carbamates

A variety of allyl carbamates (A–K, Table 1) are prepared by reacting allyl alcohol propoxylates with multifunctional isocyanates as listed in Table 1. A small amount of excess allyl alcohol propoxylate is used to convert essentially all of the isocyanate groups into carbamates. Propylene glycol methyl ether acetate (PMAc) is used as a reaction solvent in 20% of the total reactor charge. Complete conversion of the isocyanate is confirmed by IR analysis. A small amount of catalyst (stannous octoate) is used in some reactions. The solvent is removed from the product to examine the physical state and measure $T_g$. The results are summarized in Table 1.

EXAMPLE 2

Preparation of Air-drying Coating

A clear coating is prepared by mixing Carbamate B from Example 1 (35 g), n-butyl acetate (15 g) and 10% Cobalt CK (0.15 g, air-drying catalyst, product of Condea Servo). The coating is applied on steel panels with 1.5 mil of wet thickness. The panels are dried in the air at 25° C. for 7 days and properties and weathering stability are then measured. The testing results are listed in Table 2.

EXAMPLE 3

Preparation of Air-drying Coating

Example 2 is repeated but the catalyst is changed. Ser-Ad FS530 (0.43 g, air-drying catalyst, product of Condea Servo) is used. The coating properties and weathering stability are listed in Table 2.

EXAMPLE 4

Preparation of Air-drying Coating

Example 2 is repeated but the catalyst is changed. Cobalt octoate (0.43 g, air-drying catalyst, product of Condea Servo) is used. The coating properties and weathering stability are listed in Table 2.

TABLE 1

Preparation of Allyl Carbamates

| # | Alcohol | Isocyanate | Catalyst | Temp °C. | React. Time, hr | Phys. State, Neat, @25° C. | $T_g$, °C. | Visc. 80% in PMAc @25° C. |
|---|---------|-----------|----------|----------|-----------------|----------------------------|-----------|---------------------------|
| A | AP1.0[1] | HDI Trimer | None | 125 | 2 | Liquid | — | 1,980 |
| B | AP1.0 | HDI Biuret | None | 125 | 4 | — | — | 5,101 |
| C | AP1.0 | HDI Biuret | Stannous Octoate | 100 | 0.75 | — | — | 4,625 |
| D | AP2.0[2] | HDI Trimer | Stannous Octoate | 130 | 23 | Liquid | — | — |
| E | AP1.0 | Mixture of 62% IPDI and 38% IPDI Trimer | None | 148 | 24 | Liquid | — | 2,320 |
| F | AP1.0 | Mixture of 62% IPDI and 38% IPDI Trimer | Stannous Octoate | 100 | 2 | Liquid | — | 2,050 |
| G | AP2.0 | HDI Biuret | Stannous Octoate | 94 | 2 | Liquid | — | 7,009 |
| H | AP2.0 | Mixture of 62% IPDI and 38% IPDI Trimer | Stannous Octoate | 88 | 4 | Liquid | — | 225 |
| I | Allyl Alcohol | IPDI Trimer | Stannous Octoate | 85 | 2 | Solid | >50 | — |
| J | AP1.0 | IPDI Trimer | Stannous Octoate | 96 | 7 | Solid | 50 | — |
| K | AP1.0 | HDI Allophanate | — | — | — | Liquid | — | 602 |

[1]AP1.0: allyl monopropoxylate.
[2]AP2.0: allyl propoxylate having an average of about 2 oxypropylene units.

TABLE 2

Properties of Air-drying Coatings

|  | Ex. 2 | Ex. 3 | Ex. 4 |
| --- | --- | --- | --- |
| Formulation, g | | | |
| Carbamate B | 35 | 35 | 35 |
| n-Butyl Acetate | 15 | 15 | 15 |
| 10% Cobalt CK* | 0.15 | — | — |
| Ser-Ad FS530* | — | 0.43 | — |
| 12% Cobalt Octoate* | — | — | 0.15 |
| Coating Properties | | | |
| Final Dry Time, hr | 8 | 8 | 12 |
| Pencil Hardness | H | F | H |
| Koenig Hardness | 41 | 22 | 22 |
| Impact (front), in-lb | 140 | 140 | 140 |
| Impact (reverse), in-lb | 100 | 100 | 100 |
| Crosshatch Adhesion | 100% | 100% | 100% |
| MEK Rubs | >100 | 45 | >100 |
| Weathering Stability, Tested Under QUV-B | | | |
| Gloss @ 60° | | | |
| Initial | 93 | 92 | 93 |
| After 650 hrs | 95 | 94 | 93 |
| Gloss @ 20° | | | |
| Initial | 86 | 85 | 82 |
| After 650 hrs | 89 | 85 | 79 |
| Yellowness After 650 hrs | 4.3 | 3.0 | 3.7 |

*Air-drying catalysts, products of Condea Servo.

EXAMPLE 5

Preparation of UV-curable Coating

A solid unsaturated polyester resin is prepared from 3.4 moles of terephthalic acid, 7.3 moles of fumaric acid, 6 moles of ethylene glycol, and 5.2 moles of neopentyl glycol. The molecular weight of the resin is 3290 by GPC analysis. It has an acid number of 19 mg KOH/g. The resin is dissolved in tetrahydrofuran (THF) at 50% solids. Carbamate I from Example 1 is added to the polyester solution in a 1/1 weight ratio of polyester to carbamate. A photoinitiator, KIP 100F (3 wt % based on the total solids, product of Fratelli Lamberti) is added to the solution. The coating is applied to steel panels at a wet thickness of 3 mils, dried at 50° C. for 10 minutes, and cured in four passes with a single 120 W/cm UV lamp at 50 ft/min. Acetone rubbing is used to measure the curing. The panels have less than 50 acetone rubs right after curing, but 50 rubs after 24 hours.

EXAMPLES 6–8

Preparation of UV-curable Coatings

Example 5 is repeated but using a variety of photoinitiators as listed in Table 3. The acetone rubbing test results are also shown in Table 3.

TABLE 3

UV-Curable Coatings

| Ex. | Photoinitiator | Loading of Photoinitiator | Acetone Rubs After Cure | Acetone Rubs After 24 Hours |
| --- | --- | --- | --- | --- |
| 5 | KIP 100F[1] | 3 wt % | <50 | 50 |
| 6 | Irgacure 819[2] | 5 wt % | <50 | >50 |
| 7 | Darocur 4265[3] | 5 wt % | <50 | >50 |
| 8 | Irgacure 1800[4] | 5 wt % | 50 | >50 |

[1]Polymer-bound α-hydroxyalkylphenone, product of Fratelli Lamberti.
[2]Acylphosphine oxide, product of Ciba-Geigy.
[3]Blend of α-hydroxyalkylphenones, product of Merck.
[4]Acylphosphine oxide, product of Ciba-Geigy.

We claim:

1. An allyl carbamate which is a reaction product of
   (a) an isocyanate selected from the group consisting of hexaniethylene diisocyanate (HDI), HDI biuret, HDI dimer HDI trimer, HDI allophanate, isophorone diisocyanate (IPDI), IPDI trimer, IPDI allophanate, bis(isocyanatocyclohexyl)methane, and mixtures thereof and
   (b) an alkoxylated allylic alcohol having the structure of

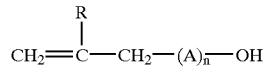

in which R is hydrogen, a $C_1$ to $C_{10}$ alkyl group, or a $C_6$ to $C_{10}$ aryl or alkylaryl group, A is a $C_2$–$C_4$ oxyalkylene group, and n, which is the average number of oxyalkylene units, has a value within the range of about 1 to about 5; wherein the allyl carbamate has at least two allyl functional groups per molecule and is a liquid at 25° C.

2. The allyl carbamate of claim 1 wherein the oxyalkylene group is selected from oxypropylene, oxyethylene, oxybutylene, and mixtures thereof.

3. The allyl carbamate of claim 1 wherein the alkoxylated allylic alcohol is propoxylated allyl alcohol.

* * * * *